United States Patent [19]
Stone

[11] Patent Number: 6,110,209
[45] Date of Patent: *Aug. 29, 2000

[54] METHOD AND PASTE FOR ARTICULAR CARTILAGE TRANSPLANTATION

[76] Inventor: Kevin R. Stone, 1 Throckmorton La., Mill Valley, Calif. 94941

[ * ] Notice: This patent is subject to a terminal disclaimer.

[21] Appl. No.: 09/187,283

[22] Filed: Nov. 5, 1998

Related U.S. Application Data

[63] Continuation-in-part of application No. 08/908,685, Aug. 7, 1997, Pat. No. 5,964,805.

[51] Int. Cl.$^7$ ............................... A61F 2/28; A61F 2/30; A61B 17/56

[52] U.S. Cl. .................................. 623/16.11; 623/23.63; 128/898

[58] Field of Search ................................ 623/11, 13, 16, 623/17, 901, 66, 20, 18; 128/898

[56] References Cited

U.S. PATENT DOCUMENTS

| | | | |
|---|---|---|---|
| 4,573,838 | 3/1986 | Omi et al. | 408/204 |
| 4,585,585 | 4/1986 | Waite | 260/112.5 R |
| 4,595,713 | 6/1986 | St. John | 623/16 |
| 4,642,120 | 2/1987 | Nevo et al. | 623/16 |
| 4,846,835 | 7/1989 | Grande | 623/11 |
| 4,895,146 | 1/1990 | Draenert | 128/754 |
| 4,971,952 | 11/1990 | Bentz et al. | 514/12 |
| 5,002,071 | 3/1991 | Harell | 128/897 |
| 5,041,138 | 8/1991 | Vacanti et al. | 623/16 |
| 5,067,963 | 11/1991 | Khouri et al. | 623/16 |
| 5,067,964 | 11/1991 | Richmond et al. | 623/18 |
| 5,082,803 | 1/1992 | Sumita | 623/16 |
| 5,092,887 | 3/1992 | Gendler | 623/13 |
| 5,281,422 | 1/1994 | Badylak et al. | 623/13 |
| 5,290,558 | 3/1994 | O'Leary et al. | 623/16 |
| 5,372,821 | 12/1994 | Badylak et al. | 623/13 |
| 5,445,833 | 8/1995 | Badylak et al. | 623/11 |
| 5,510,396 | 4/1996 | Prewett et al. | 623/16 |
| 5,554,389 | 9/1996 | Badylak et al. | 424/558 |
| 5,556,399 | 9/1996 | Huebner | 606/80 |
| 5,556,429 | 9/1996 | Felt | 623/16 |
| 5,573,784 | 11/1996 | Badylak et al. | 424/551 |
| 5,612,028 | 3/1997 | Sackier et al. | 424/93.7 |
| 5,632,747 | 5/1997 | Scarborough et al. | 606/79 |
| 5,655,546 | 8/1997 | Halpern | 128/898 |
| 5,681,353 | 10/1997 | Li et al. | 623/18 |
| 5,736,396 | 4/1998 | Bruder et al. | 435/366 |
| 5,749,874 | 5/1998 | Schwartz | 606/75 |
| 5,842,477 | 12/1998 | Naughton et al. | 623/11 |

OTHER PUBLICATIONS

Thomas Minas, MD, Current Concepts in the Treatment of Articular Cartilage Defects, SynerMed, Genzyme Tissue Repair, Cambridge, MA USA, pp. 1–12 (Sep. 1996).

Carticel© Service, Cultured Autologous Chondrocytes for Implantation, Genzyme Tissue Repair, Cambridge, MA USA, pp. 1–7 (Jan. 30, 1997).

Carticel$^{SM}$ Service, Autologous Chondrocyte Implantation, Genzyme Tissue Repair, Cambridge, MA USA, vol. #1, Cartilage Repair Registry—Sep., 1996, pp. 1–2.

Carticel$^{SM}$ Service, Recommended Indications for Cultured Autologous Chondrocyte Implantation and Average Patient Treated with Cultured Autologous Chondrocyte Implantation, Genzyme Tissue Repair, Cambridge, MA USA, Feb. 1997.

Kevin R. Stone, MD et al., Surgical Technique for Articular Cartilage Transplantation to Full–Thickness Cartilage Defects in the Knee Joint, Operative Techniques in Orthopaedics, vol. 7, No. 4 (Oct.), 1997, pp. 305–311.

S. Kadiyala et al., Culture Expanded Canine Mesenchymal Stem Cells Possess Osteochondrogenic Potential In Vivo and In Vitro, Cell Transplantation, vol. 6, No. 2, pp. 125–134, 1997.

Scott P. Bruder et al., Growth Kinetics, Self–Renewal, and the Osteogenic Potential of Purified Human Mesenchymal Stem Cells During Extensive Subcultivation and Following Cryopreservation, Journal of Cellular Biochemistry, 64:278–294 (1997).

T. Abe et al., Accelerated Repair of Full–Thickness Articular Cartilage Defects with Single Intraarticular Injection of Liposomal Transforming Growth Factors, 44$^{th}$ Annual Meeting, Orthopaedic Research Society, Mar. 18–19, 1998, New Orleans, Louisiana, p. 380.

K. Spindler et al., The Biomechanical Response to Doses of TGF–BETA A2 in the Healing Rabbit MCL, 44$^{th}$ Annual Meeting, Orthopaedic Research Society, Mar. 18–19, 1998, New Orleans, Louisiana, p. 1023.

*Primary Examiner*—Michael J. Milano
*Assistant Examiner*—Choon P. Koh
*Attorney, Agent, or Firm*—McDermott, Will & Emery

[57] ABSTRACT

The invention disclosed is a method and material for repairing focal arthritic defects in a mammalian joint, especially in a human knee. The invention disclosed provides an articular cartilage cancellous bone paste in an effective amount for enhancing formation of cartilage. The paste can include a cartilage-stimulating factor.

7 Claims, 5 Drawing Sheets

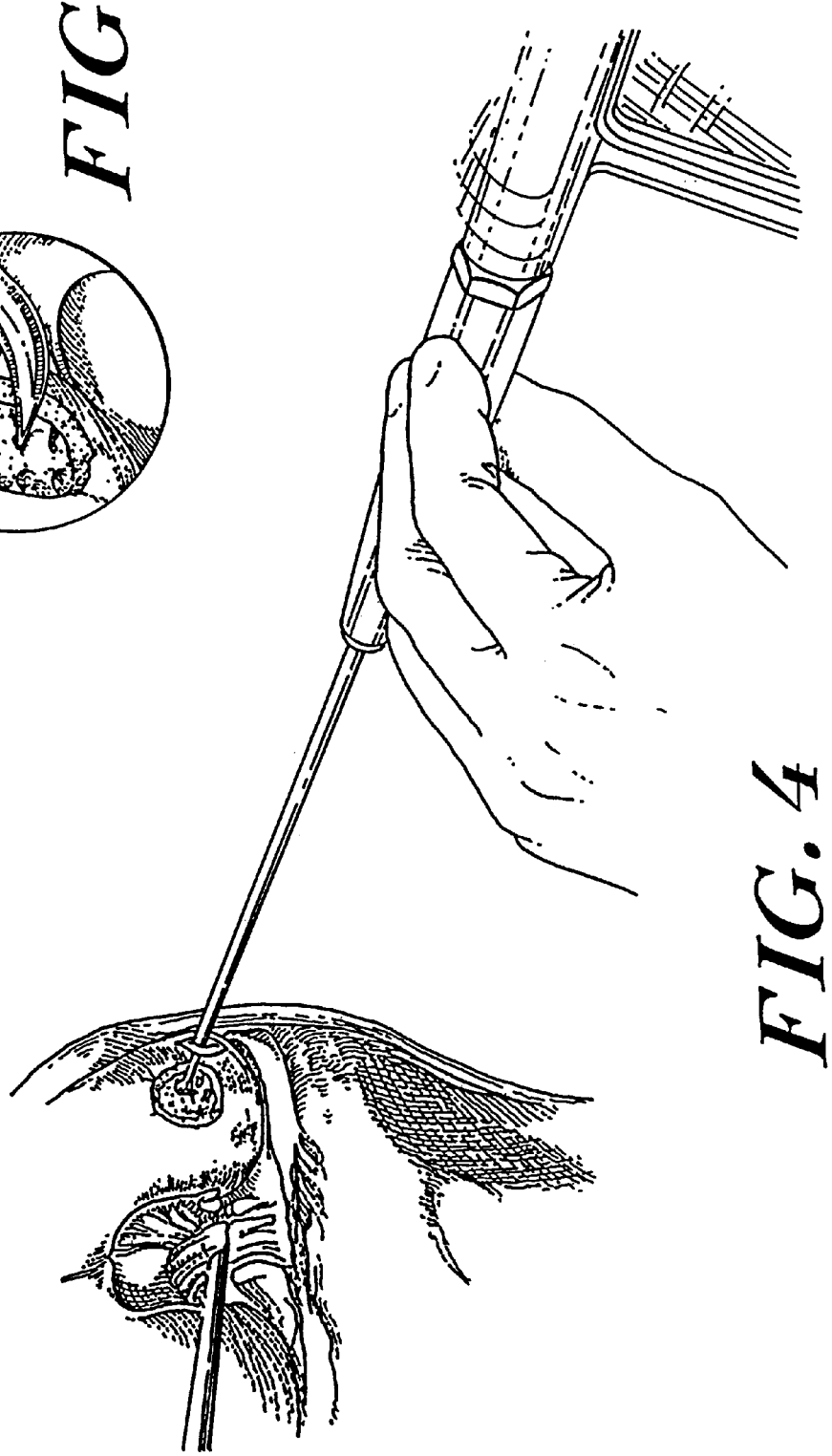
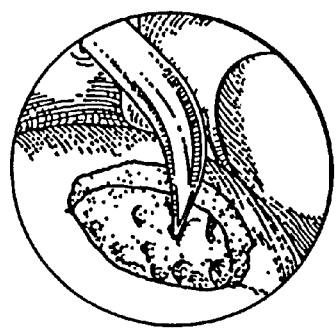
FIG. 4A
FIG. 4

METHOD AND PASTE FOR ARTICULAR CARTILAGE TRANSPLANTATION

This is a continuation-in-part of application Ser. No. 08/908,685, filed Aug. 7, 1997, now U.S. Pat. No. 5,964,805.

The present invention relates to the field of surgical methods and instruments for treatment of a focal arthritic defect in a joint of a mammal, and more particularly, for treatment of focal arthritic defects in the knee of a mammal.

REFERENCE TO RELATED APPLICATION

This application is related to U.S. patent application Ser. Nos. 08/710,176, 08/797,973 and 08/908,685.

BACKGROUND OF THE INVENTION

Focal arthritic defects are defined as areas of complete hyaline cartilage loss exposing the underlying bone ringed by areas of intact hyaline cartilage. Focal arthritic defects may occur as the result of trauma or other conditions, such as loss of the protective meniscus cartilage or osteoarthritis. Focal arthritic defects may occur in any joint, being especially problematic in the weight-bearing joints, i.e., in the hip, the knee, and the ankle. Focal arthritic defects in these joints lead to pain, swelling, and loss of motion. In the past, treatment of focal arthritic defects has included drilling, abrasion, periosteal covering and bone grafting.

SUMMARY OF THE INVENTION

The present invention provides a surgical technique in which an osteocartilaginous plug, or graft, can be removed from one location within a mammalian joint and moved to another location within the joint, or to another joint, to fill a focal arthritic defect. In one embodiment, the invention provides a method of repairing an arthritic defect in a mammalian joint which comprises the steps of forming a roughened, bleeding surface of cancellous bone within the defect; forming a plug of osteocartilaginous tissue from an undamaged site within the joint or from another joint; removing the plug from the undamaged site; crushing and mixing the plug of cartilaginous tissue to form a paste or grout; and inserting the paste into the defect, positioning the paste against the roughened bleeding surface (and optionally applying an external force to hold the paste in place) for a time sufficient to allow a blood clot to form between said plug and said roughened bleeding surface.

The invention maybe advantageously performed with an instrument set of the type described in U.S. patent application Ser. No. 08/797,973, supplemented with a press, or other device, for crushing the articular cartilage and cancellous bone plug. The instrument set preferably includes a coring device and two obturators. The first obturator is used with a coring device (or trephine) to harvest articular cartilage and cancellous bone from a site within the intercondylar notch, and the second obturator is used with a coring device to transplant the harvested articular cartilage and cancellous bone.

The invention provides the above-referenced paste formed of osteocartilaginous tissue mixture in an effective amount for enhancing the formation of cartilage. The paste can include particles of crushed cancellous bone mixed with articular cartilage. Further, the paste can include a proteinaceous factor which stimulates the formation of cartilage.

In one embodiment, the invention provides an articular cartilage paste for effecting in vivo formation of cartilage.

As used herein, the term "for effecting in vivo formation of cartilage" means that the paste provides a physical structure to which cartilage-forming cells and undifferentiated mesenchymal cells, and cartilage extracellular matrix components such as collagen fibers and proteoglycans can adhere as well as the necessary environment to signal cartilage-forming cells to produce cartilage.

BRIEF DESCRIPTION OF THE DRAWINGS

For a fuller understanding of the nature and the objects of the invention, reference should be made to the following detailed description and the accompanying drawings in which like reference numerals refer to like elements and in which:

FIGS. 3–7 illustrate a method of use of an instrument set embodying the invention.

DESCRIPTION OF THE PREFERRED EMBODIMENT

Figure 1:
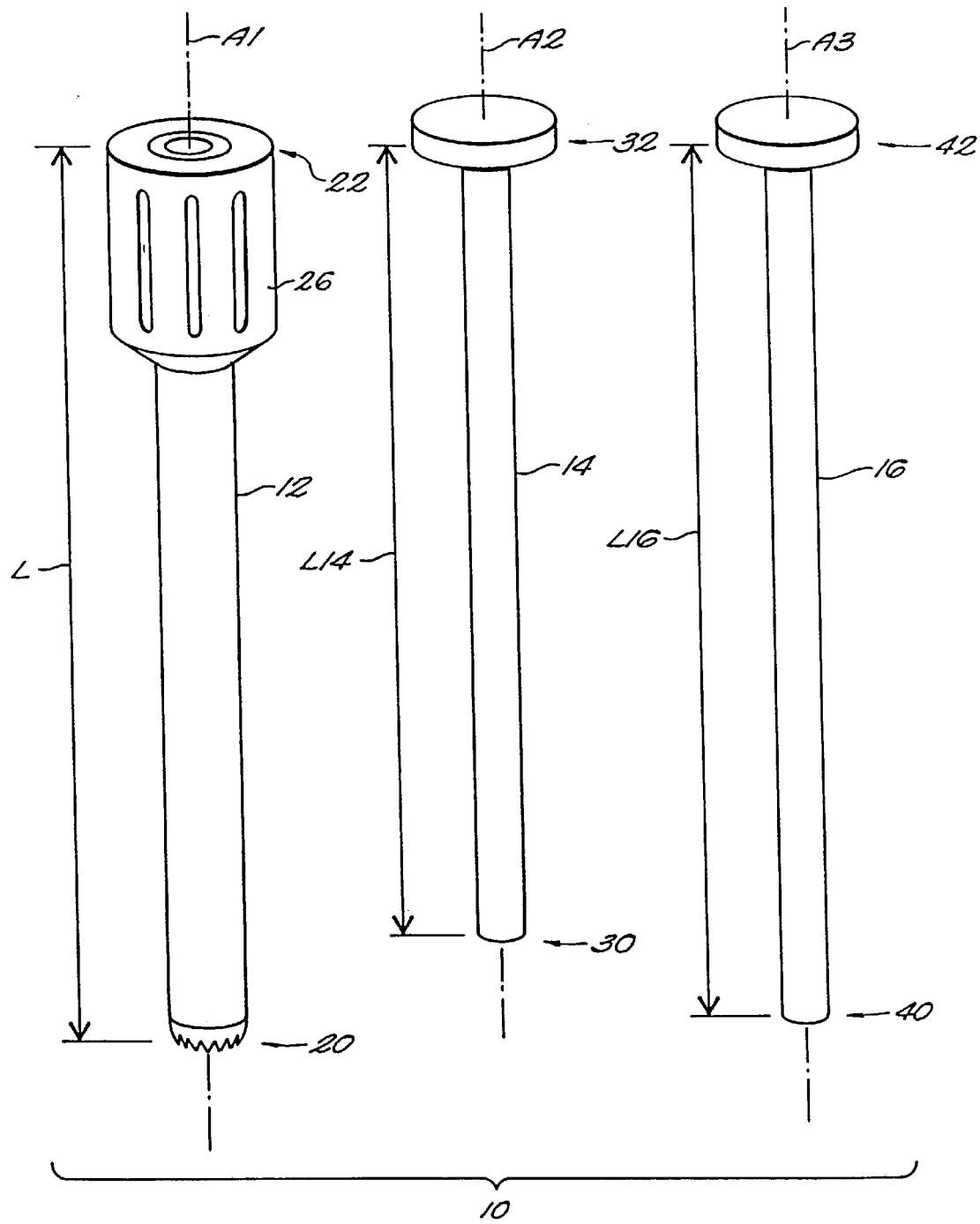
FIG. 1 shows, in perspective view, an instrument set embodying the invention.

The method and/or articular cartilage paste of the invention is suitable for repairing any arthritic defect in any joint, so long as the defect is not so extensive that no undamaged portion of the joint remains. Preferably, the method and/or paste of the invention is used to repair focal arthritic defects in the hip. More preferably, the method and/or paste of the invention is used to repair focal arthritic defects in the ankle. Most preferably, the method and/or paste of the invention is used to repair focal arthritic defects in the knee. Focal arthritic defects in the joints of any mammal may be repaired in accordance with the method and/or with the paste of the invention. Preferably, focal arthritic defects in the joints of humans may be repaired using the method and/or paste of the invention.

For example, when the joint being repaired is a knee, after routine arthroscopic examination has been performed and a focal arthritic defect has been identified, the procedure is performed as follows, preferably using an instrument kit comprising an arthroscopic awl (similar to an ice pick), one or more trephines, each with an associated obturator (or plunger) adapted to slide into the central region of its associated trephine.

The base of the arthritic defect where the exposed bone is visualized and then prepared by fracturing with the arthroscopic awl, thereby establishing a bleeding, roughened bed of cancellous bone. Preferably, the fracture holes are approximately 5–10 mm deep, with an inter-hole spacing in the range 1–5 mm, and most preferably 2–3 mm. The blood forms clots over the roughened bed exposed by the fracturing. Attention is next turned to the intercondylar notch between the two femoral condyles. Within the notch lies the anterior and posterior cruciate ligaments. The area anterior to the anterior cruciate ligament on the medial wall of the lateral femoral condyle is exposed with a curette, removing overlying soft tissue. A metal trephine coring device is then manually bored into the osteocartilaginous surface in that area down into the underlying cancellous bone to establish and capture an osteocartilaginous graft in the distal tip of the trephine coring device. Preferably, the graft is a 1 cm long by 5 mm diameter cylindrical plug weighing on the order of 0.25 grams. The trephine is then backed out of the knee joint. An obturator is introduced into the proximal end of the trephine and advanced to force the graft out of the distal end of the trephine. The graft is then placed into a graft crushing device, such as a press, where it is crushed, or morselized, to form a paste-consistency agglomerate (a "tissue paste") of crushed cancellous bone and mixed articular cartilage. The agglomerate is then loaded into the distal tip of a trephine, which tip is then positioned adjacent to the prepared bed of the arthritic defect. The plunger is introduced into the proximal end of the trephine and advanced to push the agglomerate from the trephine into the defect, where it is held in place, preferably for a period on the order of three minutes. During that time, blood clots on the roughened bed secure the graft to the bed. The instruments are then removed and the patient kept non weight-bearing for four weeks.

In one form of the invention, prior to insertion, the osteocartilaginous graft may be exposed to a proteinaceous factor which stimulates the formation of cartilage. Any cartilage-stimulating factor may be used in this embodiment, so long as the factor is capable of increasing the amount or rate of formation of cartilaginous tissue within a joint. For example, the graft may be exposed to a cartilage-stimulating factor belonging to the transforming growth factor-$\beta$ (TGF-$\beta$) supergene family. Other cartilage-stimulating factors which can be used in accordance with the present invention include, but are not limited to, analogs of such cartilage-stimulating factors having the biological activity of the corresponding natural cartilage-stimulating factor. Such a cartilage-stimulating factor may be in homodimeric or heterodimeric form. The cartilage-stimulating factor may be purified from mammalian tissue or it may produced recombinantly from one or more cDNAs encoding a monomer of the cartilage-stimulating factor. The osteocartilaginous graft can also contain more than one type of cartilage-stimulating factor in any combination.

The graft is exposed to and optionally, intermixed with, an effective amount of the cartilage-stimulating factor. As used herein, an "effective amount" of cartilage-stimulating factor means the total amount of cartilage-stimulating factor sufficient to show a meaningful patient benefit, i.e., to enhance formation of cartilage in the vicinity of the graft. Preferably, the graft is exposed to and/or intermixed with the cartilage stimulating factor, such as, for example, a cartilage-stimulating factor belonging to the transforming growth factor-$\beta$ (TGF-$\beta$) supergene family, in an amount ranging from about 0.1 ug/ml to about 1.0 ug/ml.

The cartilage-stimulating factor in free form can be administered directly to the defect site. Alternatively, the cartilage-stimulating factor can be contained within a bioabsorbable and non-toxic carrier such as a liposome and administered to the defect site. The graft is then exposed to the cartilage-stimulating factor as the cartilage-stimulating factor elutes from the carrier. The carrier can be selected to release the cartilagestimulating factor at a predetermined rate to achieve the effective amount of the cartilagegrowth stimulating factor to enhance formation of cartilage in the vicinity of the graft.

Further, the cartilage-stimulating factor can be mechanically intermixed with the paste-like agglomerate form of the graft either after transplantation has occurred or preferably, prior to transplantation. The cartilage-stimulating factor can be in its free form or contained within a liposome prior to such intermixing.

In another form of the invention, prior to insertion, the osteocartilaginous graft is exposed to and optionally, intermixed with, added cells such as undifferentiated mesenchymal stem cells and/or chondrocytes to enhance formation of cartilage in the vicinity of the graft. The mesenchymal stem cells can be obtained from blood or bone marrow. The chondrocytes can be cloned from the patient's own articular cartilage or allograft.

The graft is exposed to and/or intermixed with an effective amount of the added cells. Similar to the effective amount of cartilage-stimulating factor described above, as used herein, an "effective amount" of added cells means the total amount of these cells sufficient to show a meaningful patient benefit, i.e., to enhance formation of cartilage in the vicinity of the graft. Preferably, the graft is exposed to and/or intermixed with the added cells in an amount of about $5 \times 10^6$ cells/ml.

The cells can be mechanically intermixed with the paste-like agglomerate form of the graft either prior to transplantation or after transplantation has occurred.

Further, a biological glue can be used to fix the paste-like agglomerate form of the graft, the cartilage-stimulating factor and/or the mesenchymal and/or other cartilage forming cells to the defect site. As used herein, the biological glue is an adhesion molecule, or adhesive portion or analog thereof, which aids in cartilage regeneration by providing a tacky surface to which cartilage forming cells, cartilage fibers and/or cartilage stimulating factors can stick. The biological glue can be administered directly to the defect site. The biological glue can also be intermixed with the paste-like agglomerate form of the graft, the cartilage-stimulating factor and/or the cells either prior to transplantation or after transplantation has occurred. The biological glue includes, but is not limited to, fibrin glue; mussel glue, such as mussel glue containing bioadhesive polyphenolic proteins derived from several species of the mussel genus Mytilus (see e.g., U.S. Pat. No. 4,585,585); chondronectin; osteonectin; and fibronectin and arginine-glycine-aspartic acid (RGD) peptide (see e.g., U.S. Pat. No. 5,681,353), a portion of which can be conjugated to, for example, chondroitin sulfate, and the like.

Figure 2:
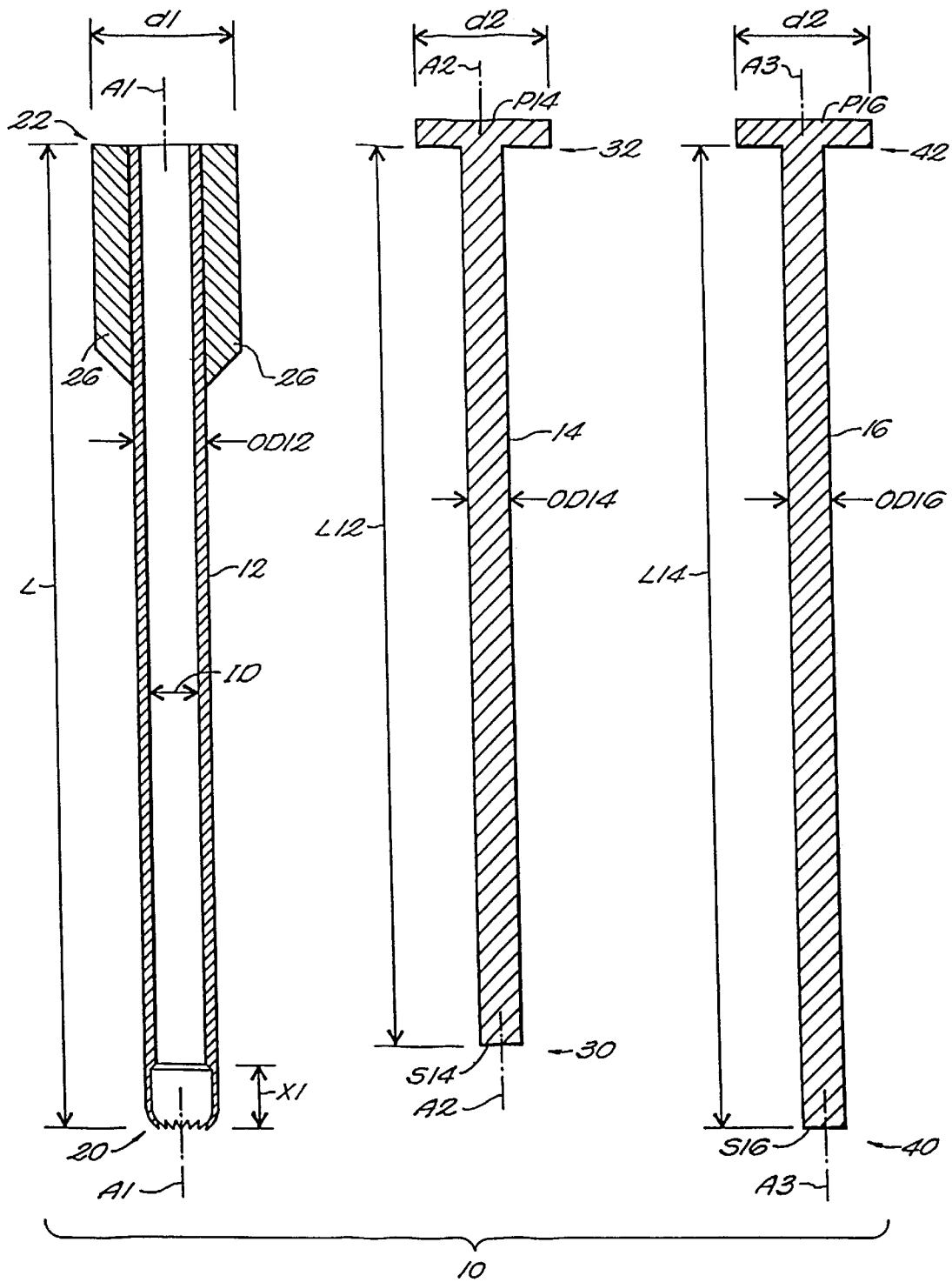
FIG. 2 shows, in sections, the instrument set of FIG. 1.

The method of the invention is preferably implemented using the articular cartilage instrument set 10 illustrated in FIGS. 1 and 2. The set 10 includes a coring device 12 and a first obturator and a second obturator 16. The coring device 12 includes a cylindrical tube extending a distance along a coring axis A between a distal end 20 and a proximal end 22. A set of cutting elements 23, or teeth, are disposed at the distal end 12, and a gripper receiving is at the proximal end. A gripper 26 extends transverse to the axis A1 near the proximal end. In the illustrated embodiment, the gripper is in the form of a cylindrical shell extending about the proximal end to tube 12 (but other forms may be used) which permits a surgeon to grip the coring device 12 with his hand and reciprocally rotate that element about axis Al and apply an axial force in the direction of axis A1.

The obturators 14 and 16 each include cylindrical rods extending along a respective one of obturator axes A2 and A3 between said distal ends 30, 40 and proximal ends 32, 42 respectively. Each of the rods has a surface S14, S16 at its distal end which extends at least partially transverse to the respective axes A2 and A3. In the illustrated embodiment, the surfaces S14, S16 are planar and perpendicular to axes A2, A3, but in other embodiments, different shapes may be used, e.g. convex, concave or irregular. The outer diameters OD14, OD16 of the rods are slightly less than the inner diameter ID of the tube of coring device 12 so that the obturator may be slidingly within the tube of device 12 with axes A2 and A3 being substantially coaxial with axis A1. Pusher sections P14, P16 are positioned at the proximal ends of the rods of obturators 14 and 16, respectively. The pusher sections P14, P16 have outer diameters d2 larger then ID of device 12. The pusher sections P14, P16 may have rounded ends to permit a surgeon to easily apply an axial force by hand, while gripping the gripper members 26.

The length L14 of obturator 14 is selected so that when its rod is positioned all the way into the tube of device 10, i.e. with section P14 adjacent to end 22 of tube 12 the distal end 30 of obturator 14 is displaced by distance X1 from the end 20 of device 12. The length L16 of obturator 16 is selected so that when obturator 16 is fully positioned within device 12, i.e. with section P16 adjacent to end 22 of tube 12, the end 40 of obturator 16 is substantially at (or extends beyond) the distal end 20 of device 12. Variations of the lengths L1 and L2 are within the scope of the invention. Other dimensions of the instruments are indicated by reference designators in FIG. 2. In the preferred embodiment:

L=20 cm
OD12=6 (or 11) mm
d1=20 mm
d2=20 mm
ID=4 (or 9) mm
ID2=5 (or 10) mm
X1=2 cm
L1=18 cm
L2=20 cm

FIGS. 3–7 illustrate the method of the invention, using a variant of the instrument set of FIGS. 1 and 2. In that embodiment, the tube of coring device 10 has a constant outer diameter along its length. In one form, the inner surface of the tube 12 is "rifled", i.e. has one or more helical grooves extending about the coring axis A1, near the distal end of device 12, to aid in keeping the harvested cartilage and cancellous bone in place. In another form, as illustrated in FIGS. 1 and 2, that inner surface defines a larger diameter (ID2) region near the distal end 20 than at other locations along its length.

Figure 3:
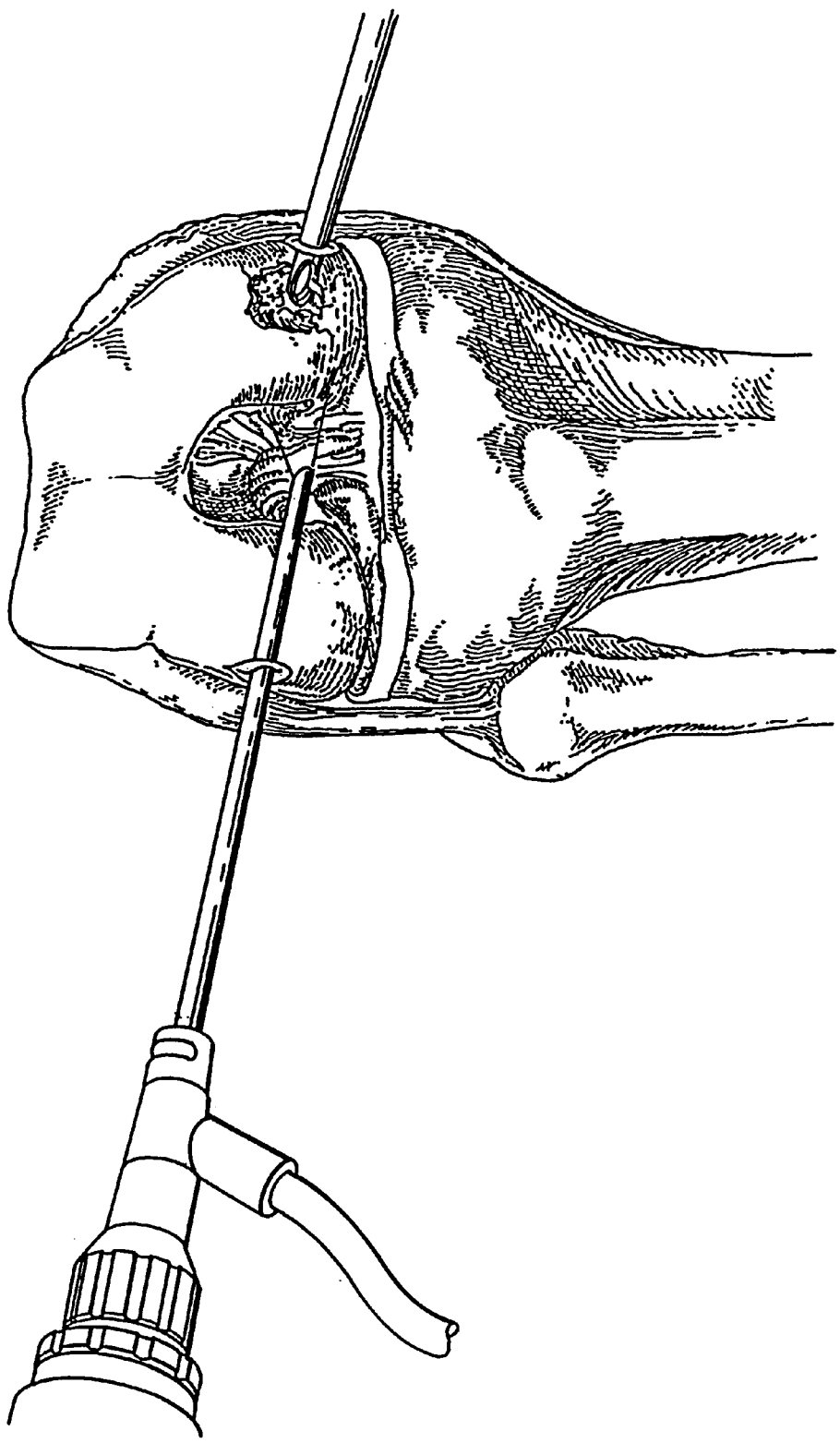
Figure 5:
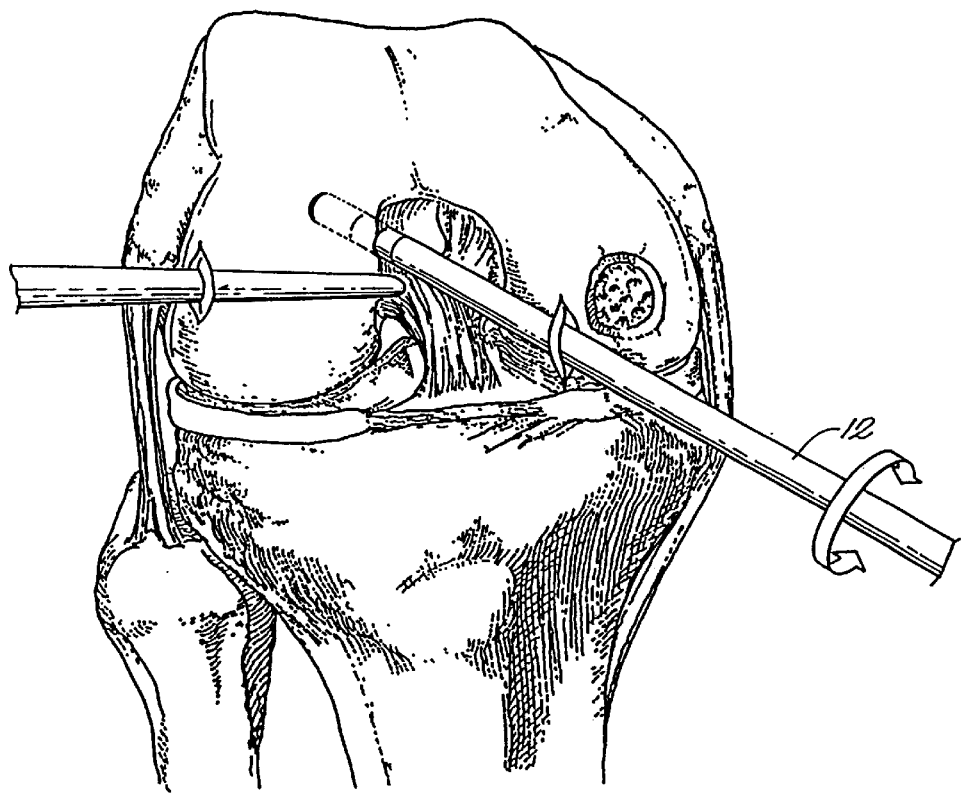
Figure 6:
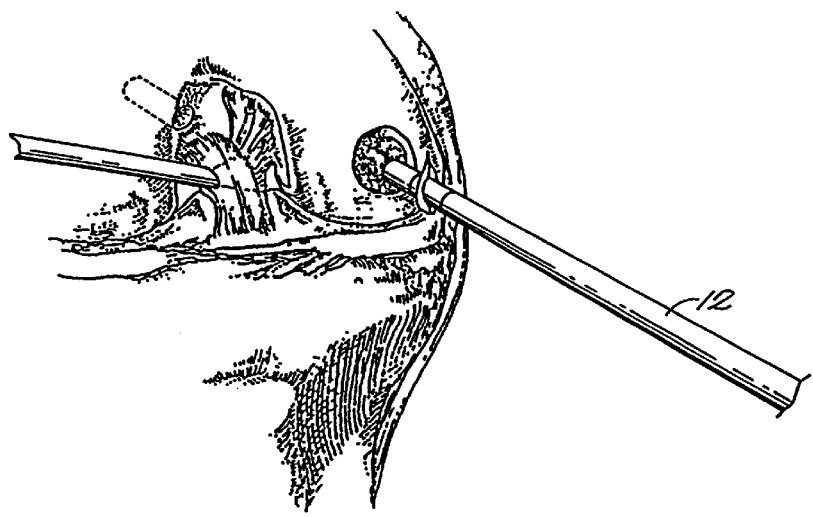
Figure 7:
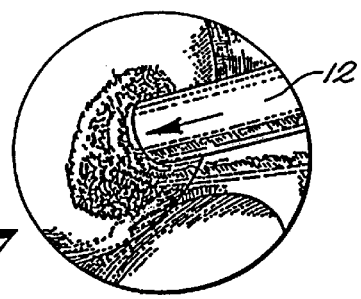

In FIG. 3, the first step of articular cartilage transplantation is shown, demonstrating shaving of articular cartilage lesion. FIG. 4 shows microfracture preparation of the base of a chondral lesion prior to articular cartilage grafting. FIG. 5 shows harvesting of articular cartilage with cancellous bone from the intercondylar notch. FIGS. 6 and 7 show transplantation of the articular cartilage and cancellous bone graft to the prepared chondral defect. In accordance with the invention, the harvested articular cartilage and cancellous bone is crushed and mixed before transplantation.

The articular cartilage paste of the present invention is formed of an osteocartilaginous tissue mixture including crushed and mixed articular cartilage and cancellous bone in an effective amount for enhancing formation of cartilage. An "effective" amount of paste, as used herein, means the total amount of paste sufficient to show a meaningful patient benefit, i.e., to enhance the formation of cartilage in the vicinity of the graft. Further, the paste can include an effective amount of cartilage-stimulating factor, as described above.

Those of skill in the art will recognize that the invention may be embodied in other specific forms without departing from the spirit or essential characteristics thereof. The presently described embodiments are therefore to be considered in all respects as illustrative and not restrictive, the scope of the invention being indicated by the appended claims rather than by the foregoing description, and all variations of the invention which are encompassed within the meaning and range of equivalency of the claims are therefore intended to be embraced therein.

What is claimed is:

1. An articular cartilage paste comprising:

an osteocartilaginous tissue mixture for effecting in vivo cartilage formation, the osteocartilaiinous tissue mixture comprising crushed articular cartilage and cancellous bone, a cartilage-stimulating factor, wherein the cartilage-stimulating factor comprises a TGF-β growth factor in an amount ranging from about 0.1 ug/ml to about 1.0 ug/ml.

2. An articular cartilage paste comprising:

an osteocartilaginous tissue mixture for effecting in vivo cartilage formation, the osteocartilaginous tissue mixture comprising crushed articular cartilage and cancellous bone, a cartilage-stimulating factor, wherein the cartilage-stimulating factor is contained within a non-toxic, bioabsorbable carrier.

3. An articular cartilage paste comprising:

an osteocartilaginous tissue mixture for effecting in vivo cartilage formation, the osteocartilaginous tissue mixture comprising crushed articular cartilage and cancellous bone, further comprising:

a plurality of cells.

4. The articular cartilage paste of claim 3 wherein the cells comprise a plurality of undifferentiated mesenchymal stem cells.

5. The articular cartilage paste of claim 3 wherein the cells comprise a plurality of cloned chondrocytes.

6. An articular cartilage paste comprising:

an osteocartilaginous tissue mixture for effecting in vivo cartilage formation, the osteocartilaginous tissue mixture comprising crushed articular cartilage and cancellous bone, further comprising:

a biological glue.

7. The articular cartilage paste of claim 6 wherein the biological glue is selected from the group consisting of fibrin glue, mussel glue, chondronectin, osteonectin, fibronectin, arginine-glycine-aspartic acid peptide, and combinations thereof.

* * * * *